July 16, 1968 D. E. BEBB Plant Pat. 2,819
DOGWOOD TREE
Filed Dec. 6, 1966
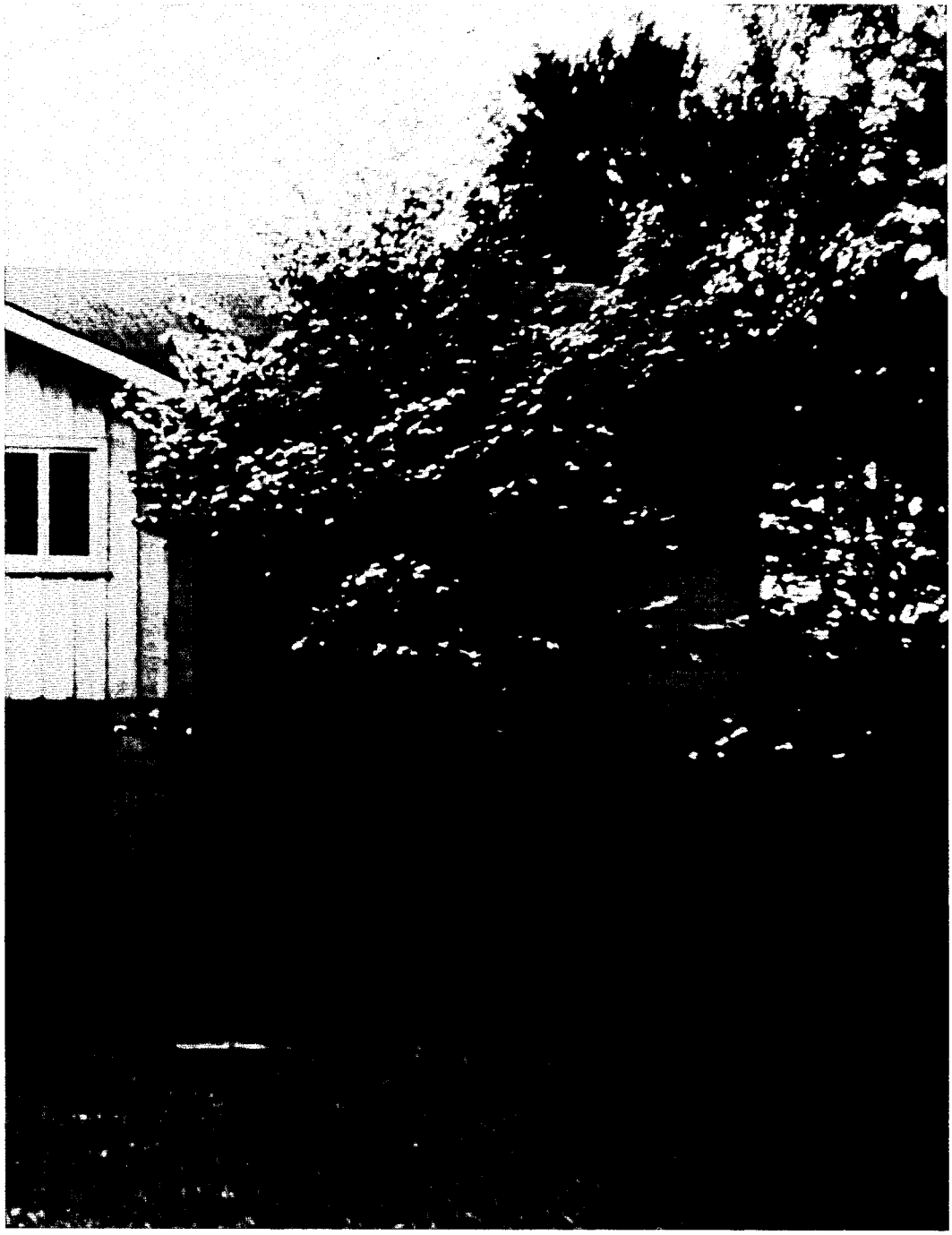
Inventor.
Douglas E. Bebb
By: Robb & Robb
Attorneys.

United States Patent Office

Plant Pat. 2,819
Patented July 16, 1968

2,819
DOGWOOD TREE

Douglas E. Bebb, Gatlinburg, Tenn., assignor to Chase Nursery Company, Inc., Chase, Ala., a corporation of Alabama

Filed Dec. 6, 1966, Ser. No. 599,654
1 Claim. (Cl. Plt.—51)

The present invention relates to a new and distinct variety of dogwood tree which was discovered by me on my cultivated property at Gatlinburg, Tenn. as a newly found seedling of unknown parentage, but apparently being a mutation of an unidentified variety of the species botanically known as *Cornus florida.*

At the time of my discovery, I had planted a number of dogwood trees on my property aforesaid at Gatlinburg, Tenn., and as they grew over the years, my attention was attracted to one particular tree by the unusual and surprising fragrance of its ffowers, resembling the fragrance of honeysuckle. I therefore continued to carefully preserve and observe this tree and in due course, I asexually reproduced the same by grafting, as performed on my property at Gatlinburg, Tenn., and also performed on my behalf by my assignee in the latter's nursery at Chase, Ala.

Continued observations and tests of the original seedling and of the progeny thereof derived by grafting as aforesaid, showed that the unique flower fragrance comes true and is established and transmitted through succeeding propagations.

The accompanying drawing shows a typical flowering tree of my new dogwood variety which generally resembles trees of the species botanically known as *Cornus florida,* except for the fact that the flowers of that species have no fragrance, while those of my new variety have a strong fragrance resembling the fragrance of honeysuckle.

The following is a detailed description of my new variety, with color terminology in accordance with the Nickerson Color Fan, published by Munsell Color Co., Inc., of Baltimore, Md., except where general color terms of ordinary dictionary significance are obvious, as based upon observations of specimens grown at Chase, Ala.:

Parentage: Unknown, but apparently a mutation of an unidentified variety of the species botanically known as *Cornus florida.*

Tree: Small; upright; low and spreading when pruned, but naturally tall under most favorable growing conditions; hardy.

*Trunk.*—Stocky; rough.

*Branches.*—Stocky; smooth. Color: one year old—Moderate Yellow Green, Plate 5GY 5/6; two years old—Strong Yellowish-Brown, Plate 7.5GY 5/7.

*Lenticels.*—Number—about 320 per average internode on 1-year old or new shoots.

*Leaves.*—Quantity—4 pairs; opposite; borne on medium size shoots; 5 pairs on average size shoots. Length—from 5¼ inches to 6¼ inches. Width—from 2½ inches to 3½ inches. Shape—ovate. Color (upper surface)—Moderate Yellow Green, Plate 5GY 5/7. Thickness—thin. Margin—smooth edge; some undulate. Petiole—short. Glands—none apparent. Stipules—none apparent.

Flower buds:

*Hardiness.*—Hardy.

*Size.*—About ¼ inch long; about ¼ inch in diameter.

*Shape.*—Flattened with small peak at apex.

*Color.*—Moderate Yellow Green Plate 5GY 5/7.

Flowers:

*Blooming habit.*—Usually varies during first 10 days in April, depending on seasonal conditions.

*Quantity.*—Normal.

*Size.*—Medium; from about 3 inches to 3½ inches wide.

*Petalage.*—Number of petals—4 (bracts). Shape of petals—ovate. Size of petals: length—about 1 inch to 1½ inches; width—about 1¼ inches. Color—yellowish-white.

*Fragrance.*—Strong, as determined by observations and tests extended over a prolonged period of 5 to 6 years. Nature—resembles fragrance of honeysuckle and apparently attributable to the stigmatic fluid.

I claim:

1. A new and distinct variety of dogwood tree, substantially as herein shown and described, characterized particularly as to novelty by its general resemblance to trees of the species botanically known as *Cornus florida,* but being uniquely distinguished therefrom by the strong fragrance of its flowers resembling the fragrance of honeysuckle.

No references cited.

ROBERT E. BAGWILL, *Primary Examiner.*